(12) United States Patent  (10) Patent No.: US 8,062,608 B2
Pankow  (45) Date of Patent: Nov. 22, 2011

(54) FLUID SEPARATOR COLLECTION CARD

(75) Inventor: Mark Lee Pankow, Chicago, IL (US)

(73) Assignee: Advance Dx, Inc., Chicago, IL (US)

(*) Notice: Subject to any disclaimer, the term of this patent is extended or adjusted under 35 U.S.C. 154(b) by 394 days.

(21) Appl. No.: 12/120,972

(22) Filed: May 15, 2008

(65) Prior Publication Data

US 2008/0286150 A1    Nov. 20, 2008

Related U.S. Application Data

(60) Provisional application No. 60/930,526, filed on May 17, 2007.

(51) Int. Cl.
  G01N 1/00   (2006.01)
  G01N 21/75  (2006.01)
  G01N 31/22  (2006.01)
  G01N 33/52  (2006.01)
(52) U.S. Cl. ........ 422/420; 422/400; 422/401; 436/176
(58) Field of Classification Search ............ None
  See application file for complete search history.

(56) References Cited

U.S. PATENT DOCUMENTS

| 4,055,394 | A |   | 10/1977 | Friedman et al. |
|---|---|---|---|---|
| 4,933,092 | A |   | 6/1990 | Aunet et al. |
| 4,943,522 | A |   | 7/1990 | Eisinger et al. |
| 4,999,285 | A | * | 3/1991 | Stiso .................... 422/58 |
| 5,064,541 | A |   | 11/1991 | Jeng et al. |
| 5,409,664 | A |   | 4/1995 | Allen |
| 5,435,970 | A |   | 7/1995 | Mamenta et al. |
| 5,547,873 | A |   | 8/1996 | Magneson et al. |
| 5,589,399 | A |   | 12/1996 | Allen et al. |
| 6,258,045 | B1 |   | 7/2001 | Ray et al. |
| 6,316,205 | B1 |   | 11/2001 | Guan et al. |
| 6,365,417 | B1 | * | 4/2002 | Fleming et al. ........... 422/58 |
| 6,465,202 | B1 |   | 10/2002 | Tyrrell |
| 6,524,533 | B1 |   | 2/2003 | Tyrrell |
| 7,115,421 | B2 |   | 10/2006 | Grzeda et al. |
| 7,268,179 | B2 | * | 9/2007 | Brown ..................... 524/548 |
| D560,811 | S |   | 1/2008 | Powell et al. |

(Continued)

FOREIGN PATENT DOCUMENTS

DE    4341005    6/1995

(Continued)

OTHER PUBLICATIONS

International Search Report of PCT/US08/63707 dated Aug. 7, 2008 (2 pages).

(Continued)

Primary Examiner — Jill Warden
Assistant Examiner — Charles D Hammond
(74) Attorney, Agent, or Firm — Maginot, Moore & Beck, LLP

(57) ABSTRACT

A device for separating and drying a fluid sample in one embodiment includes an upper layer including a sample window and a viewing window extending therethrough, the viewing window spaced apart from the sample window, an absorbent layer, having a width and a length, positioned beneath the upper layer and extending beneath the sample window and the viewing window, and a non-absorbent layer positioned beneath the absorbent layer, the non-absorbent layer having a width and a length greater than the width and the length of the absorbent layer.

20 Claims, 4 Drawing Sheets

U.S. PATENT DOCUMENTS

| | | | |
|---|---|---|---|
| 7,867,780 B2 * | 1/2011 | Jones et al. | 436/514 |
| 2002/0192835 A1 * | 12/2002 | Cho et al. | 422/56 |
| 2004/0023399 A1 * | 2/2004 | Grzeda et al. | 422/58 |
| 2006/0115805 A1 | 6/2006 | Hansen et al. | |
| 2007/0048345 A1 | 3/2007 | Huang et al. | |
| 2008/0210644 A1 | 9/2008 | Milunic et al. | |

FOREIGN PATENT DOCUMENTS

| | | |
|---|---|---|
| EP | 0183442 | 6/1986 |
| EP | 0806666 | 11/1997 |
| EP | 1387170 | 2/2004 |
| WO | WO 9641817 A1 * | 12/1996 |
| WO | 0136974 | 5/2001 |
| WO | 2006083053 | 8/2006 |

OTHER PUBLICATIONS

European Search Report in corresponding European patent application (i.e., EP 08 75 5539), dated Jul. 7, 2010 (6 pages).

EPO automated translation of DE 4341005 Description.

* cited by examiner

FLUID SEPARATOR COLLECTION CARD

This application claims the benefit of U.S. Provisional Application No. 60/930,526, filed May 17, 2007.

FIELD OF THE INVENTION

The present invention relates to collection and separation of biological fluids. More particularly the invention relates to fluid sample collection devices used for collection and separation of fluids such as blood.

BACKGROUND

Biological samples are frequently used in laboratory and clinical settings to analyze various components in the samples. The biological samples include blood samples, sputum samples, and urine samples. Such samples, for example, are used to determine the levels or concentrations of various components such as HDL, LDL, Cholesterol, hemoglobin, detection of genes using DNA or RNA along with detection of HIV antibodies, or concentrations of drugs.

The biological sample is frequently processed in a liquid form. Accordingly, the liquid sample is collected, handled by the collection facility, transported to a laboratory, and stored pending processing. Activities surrounding a liquid blood sample present various problems including the risk of container breakage or leakage which causes loss of sample and the danger of infection, sample instability during shipment and storage, transport carrier restrictions related to transport of liquid biohazard materials, and collection of significantly more sample than is necessary for testing so as to ensure sufficient sample quantity is available for common methods of serum or plasma preparation and subsequent analysis. Thus, collection of several vials of fluid such as blood from a patient is not uncommon.

In response to the shortcomings of liquid sample collection, transport, and processing, various dried sample devices and methods have emerged. In dried sample devices, a biological sample is collected in the form of a drop or two of fluid such as whole blood. The blood is collected on filter paper and allowed to dry prior to leaving the collection facility. One benefit of using dried blood samples is that dried blood samples are not classified as a special shipping required biohazard material and may be transported through the mail system or other common delivery service just as any other package.

Additionally, even when a blood or other fluid sample is removed from the body, the concentration of various components within the sample can change over time due to various ongoing reactions. For example, biochemical and cellular changes, such as red blood cells metabolizing plasma glucose for continued cellular respiration, continue in liquid samples. Additionally, when using dried whole blood collection methods, such as collection on Whatman 903 filter paper, as the blood dries, the red cells hemolyze which then becomes mixed with red blood cell membrane cholesterol. The red blood cell membrane cholesterol, which is not normally in the serum portion of the blood, then becomes mixed in with serum cholesterol. Such a mixing may yield a clinically significant increase in a patient cholesterol result. Dried fluid samples have the advantage of reducing various reactions, thereby preserving certain components for later analysis.

The transportation and handling of dried fluid samples is thus a significant improvement over transportation and handling of liquid samples. Merely drying a fluid sample does not always ensure the usefulness of the sample. By way of example, in order to perform analysis of certain dissolved blood components a whole blood sample cannot be used. For example, hemoglobin can interfere with serum analytes at the light absorbance in the instrumental step of clinical analyte testing. Accordingly, the red blood cells must first be separated from the blood plasma or serum prior to drying. The most conventional manner of separating serum or plasma from blood cells is by centrifugation. Centrifugation, of course, requires more than a few drops of blood. Additionally, expensive and space consuming equipment must be maintained at the collection site to perform centrifugation.

Various approaches have been developed to provide for separation of blood samples prior to drying of the samples. For example, U.S. Pat. No. 5,064,541, issued to Jeng et al. on Nov. 12, 1991, describes a device which separates plasma from red blood cells that uses an agglutination agent in a filter to clump red blood cells together. The incorporation of an additional biochemical filter in the device adds to the complexity and cost of the device. Additionally, the amount of blood collected may overwhelm the ability of the red blood cell agglutinating agent to work on all of the red blood cells applied in the whole blood sample.

U.S. Pat. No. 4,816,224, issued to Vogel, et al. on Mar. 28, 1989, describes a series of wicking papers and a relative large sample holder with different embodiments that contain many different components. The device is complex and requires significant foot print space when shipping or undergoing sample extraction at a remote laboratory.

U.S. Pat. No. 6,258,045, issued to Ray et al. on Jul. 10, 2001, describes a device which requires tubing for capillary collection of whole blood along with filtration and multiple layers of reactive or non-reactive materials for plasma separation and testing. Capillary collection tubes require a certain level of operator experience and inflict additional pain on the patient when compared to a simple lancet stick. Additionally, the glass tube can be broken or become detached.

Traditional devices for obtaining dried fluid samples further incorporate indirect methods for ensuring that the proper amount of fluid has been collected to allow the desired separation. Some devices incorporate an indicator which changes color or a portion of the strip which provides a chemical reaction. Such devices do not provide an indication of whether or not too large a sample of fluid has been collected.

Therefore, a collecting device that is self-contained and can be used to provide stable dried biological components to a laboratory would be beneficial. Further benefits would be realized if the device is simple to manufacture and provides accurate results. Further benefits would be provided by a device which enables both the sample collector and laboratory personal to visually directly observe the amount of fluids, such as serum or plasma or red blood cells, which have been collected. A device that can be used to separate fluids such as blood into separate components and which is easy to mail without additional charges would also be beneficial.

SUMMARY

The present invention is directed to a device for separating and drying a fluid sample. In one embodiment, a fluid sample collection card includes an upper layer including a sample window and a viewing window extending therethrough, the viewing window spaced apart from the sample window, an absorbent layer, having a width and a length, positioned beneath the upper layer and extending beneath the sample window and the viewing window, and a non-absorbent layer positioned beneath the absorbent layer, the non-absorbent layer having a width and a length greater than the width and the length of the absorbent layer.

In another embodiment, a fluid sample collection device includes an upper layer, a first rim in the upper layer defining a first window with a length and a width through the upper layer, a second rim in the upper layer defining a second window with a length and a width through the upper layer, a bridge member with a length and a width located between the first window and the second window, a non-absorbent layer with a length that is longer than the combined lengths of the first window, the second window and the bridge member, and an absorbent layer clamped between the upper layer and the non-absorbent layer by the first rim, the second rim and the bridge.

In a further embodiment, a fluid sample collection device includes an upper layer, a sample receiving portion of an absorbent layer accessible through the upper layer, a sample indicating portion of the absorbent layer viewable through the upper layer, and a non-absorbent layer with a length that is longer than the combined lengths of the sample receiving portion of an absorbent layer and the sample indicating portion of the absorbent layer, the non-absorbent layer positioned on the side of the absorbent layer opposite to the upper layer.

These and other advantages and features of the present invention may be discerned from reviewing the accompanying drawings and the detailed description of the preferred embodiment of the invention.

BRIEF DESCRIPTION OF THE DRAWINGS

The present invention may take form in various system and method components and arrangement of system and method components. The drawings are only for purposes of illustrating exemplary embodiments and are not to be construed as limiting the invention.

DESCRIPTION

Figure 1:
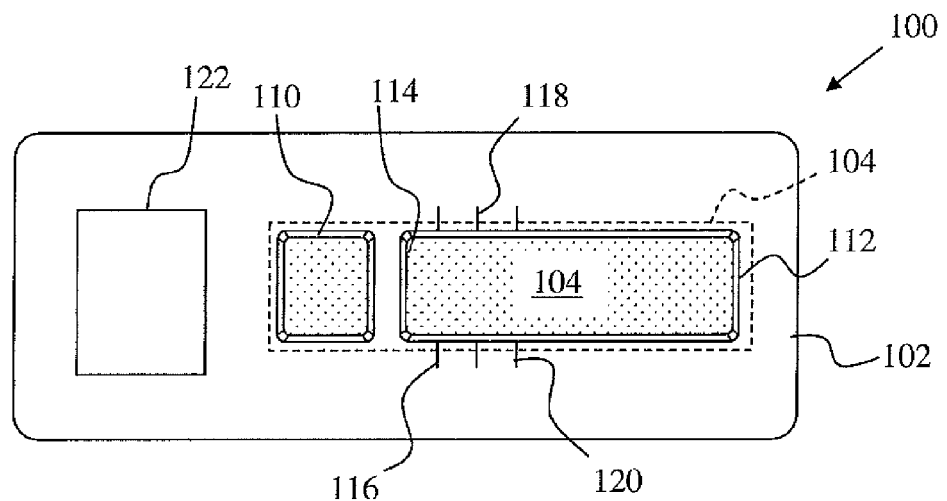
FIG. 1 depicts a top plan view of a separator card including a sample receiving portion of an absorbent layer accessible through an upper layer of the card and a sample indicating portion of the absorbent layer viewable through the upper layer of the card in accordance with principles of the invention.
Figure 2:
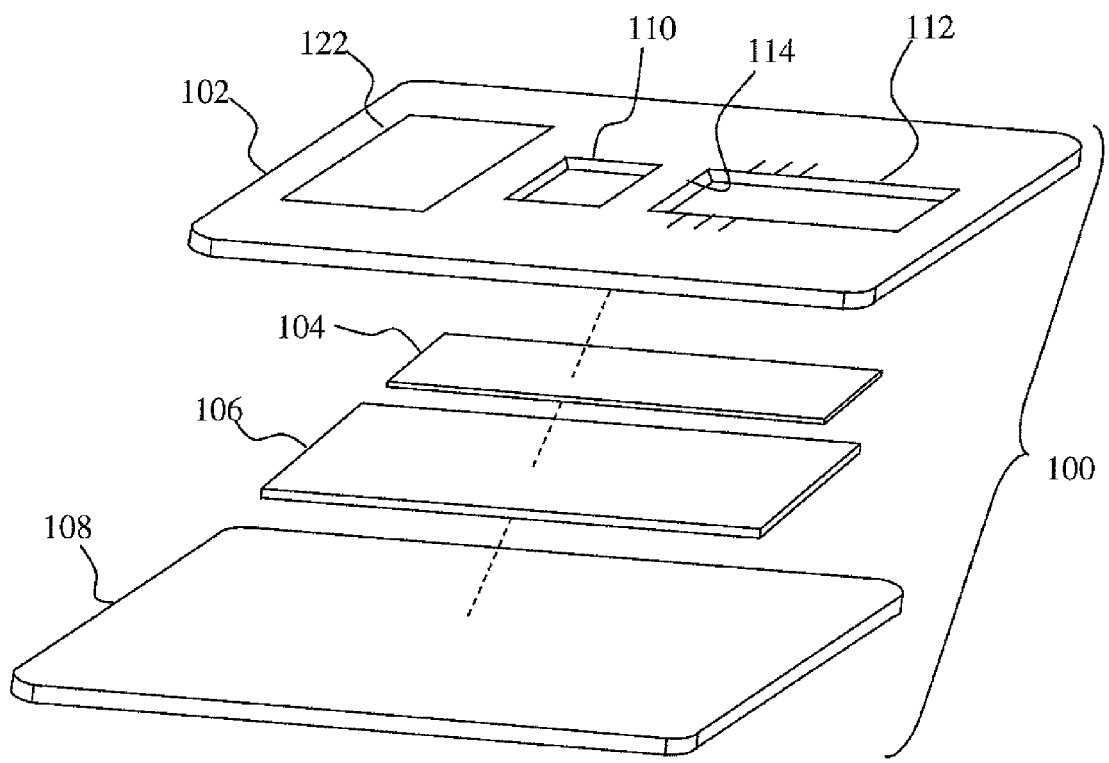
FIG. 2 depicts an exploded perspective view of the card of FIG. 1.

Referring to FIGS. 1 and 2, a separator card 100 is shown which in this embodiment is configured to separate serum and plasma in a blood sample. The separator card 100 includes an upper layer 102, an absorbent layer 104, a non-absorbent layer 106 and a support layer 108. The upper layer 102 includes a sample window 110 and a viewing window 112. A bridge 114 is located between the sample window 110 and the viewing window 112.

The upper layer 102 is fabricated from card stock. Accordingly, a user or manufacturer can easily print data on the upper layer 102. By way of example, a series of reference marks 116, 118, and 120, which extend outwardly from the sides of the viewing window 112, along with an identification block 122 are shown on the upper layer 102. Instructions for using the separator card 100 may be printed in the identification block 122 and space for insertion of patient identification data may also be provided therein.

The absorbent layer 104 is sized to be slightly longer than the length of the upper layer 102 between the outer ends of the sample window 110 and the viewing window 112 and slightly wider than the sample window 110 and the viewing window 112. The absorbent layer 104 in this embodiment is made from Whatman LF-1 material, commercially available from Whatman Inc. of Florham Park, N.J. Other suitable material may be used, such as, but not limited to, porous materials that allow liquid and suspended solids to differentially flow and separate based on the molecular size of the molecules.

Additionally, the characteristics of the absorbent layer 104 may be modified by incorporating designs that utilize other physical forces that affect the flow of substances through the absorbent layer 104. Such physical forces include hydrophobic or hydrophilic interactions as well as ionic interactions. Additionally, temporary hydrogen bonding interactions and gravitational effects may be used to augment or retard flow to provide the desired separation or alteration of a separation of the flowing liquids and suspended cells or other solid materials.

The non-absorbent layer 106 is sized to be at least slightly longer and wider than the absorbent layer 104. The non-absorbent layer 106 in this embodiment is Mylar, which is used for its imperviousness to liquid penetration. Other materials which may be used to form an acceptable liquid barrier include thin sheets of Polyethylene, porous UHMWPE film, FEP film, polyester treated sheeting and polypropylene.

Another material which provides an acceptable liquid barrier is porous ePTF film, commercially available from DeWal Industries, Inc. of Saunderstown, R.I. as product number D/W 233MS. The ePTF material is a fluoropolymer material which contains a fluorocarbon material at its surface. The fluorine molecule is the most electronegative element, thereby providing a desired hydrophobic quality. Specifically, it is believed that the fluorocarbon additive to the base plastic polymer in this material and other fluoropolymers enhances the separation of plasma from the red blood cells in the touching absorbent layer 104.

Assembly of the separator card 100 includes cutting of card stock into the shape of the upper layer 102 and the support layer 108 and forming the sample window 110 and the viewing window 112 by press stamping the upper layer 102. The upper layer 102 and the support layer 108 in this embodiment are about 10 centimeters long and about 4.5 centimeters wide.

Figure 3:
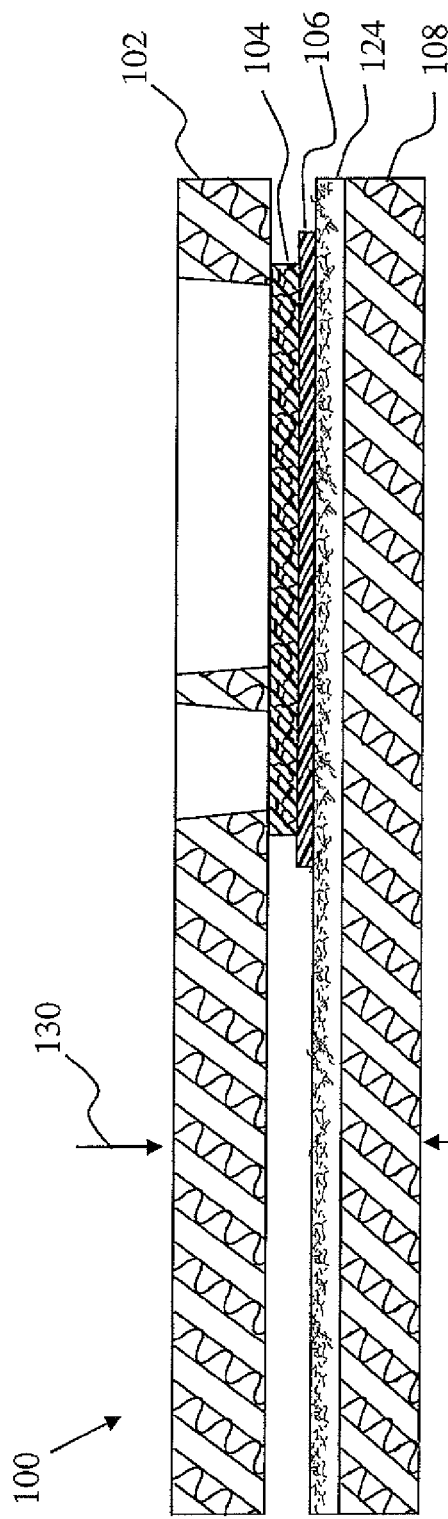
FIG. 3 depicts a side cross-sectional view of the layers of the separator card of FIG. 1 before the upper layer is attached to the support layer by an adhesive layer.

The layers of the separator card 100 may be joined by initially applying a layer of adhesive 124 (see FIG. 3) on the support layer 108. Subsequently, the non-absorbent layer 106, the absorbent layer 104 and the upper layer 102 are placed onto the support layer 108 resulting in the configuration of FIG. 3. The separator card 100 is then pressed together as indicated by the arrows 130 and 132 resulting in the configuration of FIG. 4. If desired, heat may also be applied to assist in attaching the upper layer 102 and the non-absorbent layer 106 to the support layer 108.

Figure 4:
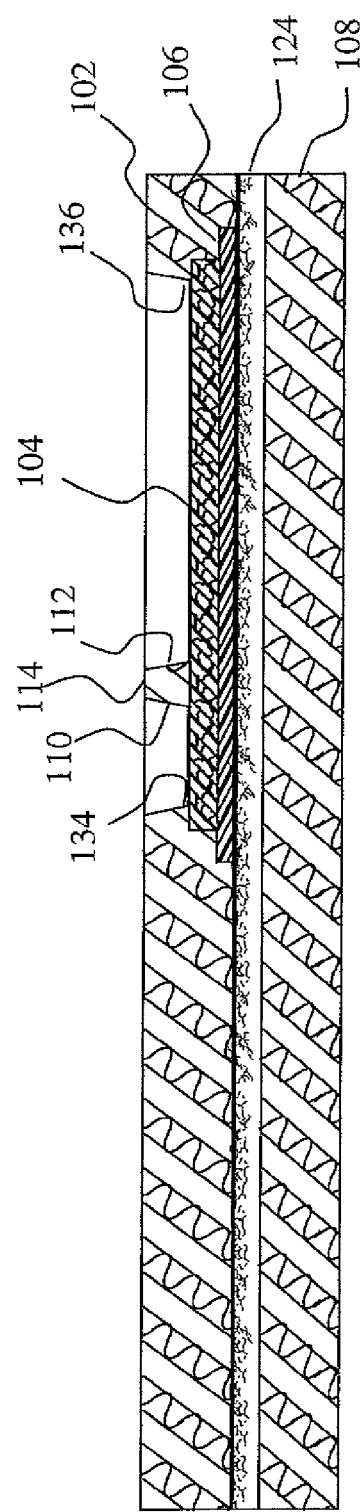
FIG. 4 depicts a side cross-sectional view of the layers of the separator card of FIG. 1 after the upper layer is attached to the support layer by an adhesive layer.

As shown most clearly in FIG. 4, the non-absorbent layer 106 is at least slightly wider and slightly longer than the absorbent layer 104. Accordingly, while the non-absorbent layer 106 is adhered to the support layer 108, the adhesive 124 does not contact the absorbent layer 104. Rather, the absorbent layer 104 is maintained in position by the upper layer 102.

Specifically, the upper layer 102 contacts the adhesive layer 124 completely around the periphery of the non-absorbent layer 106. The absorbent layer 104 is thus entrapped by a lip 134 about the sample window 110 and a lip 136 about the viewing window 112. The bridge 114 also entraps the absorbent layer 104 within the separator card 100.

Additionally, pressing of the upper layer 102 against the sandwiched layers (the absorbent layer 104 and the non-absorbent layer 106) causes deformation of the upper layer 102. The deformation includes some amount of compression of the upper layer 102 in an area of the upper layer 102 beginning with the portions of the upper layer 102 which are in contact with the absorbent layer 104 and the non-absorbent layer 106 and extending upwardly from those portions. Accordingly, the portions of the upper layer 102 which define the sample window 110 and the viewing window 112 are more impervious to fluids. The compacted areas of the upper layer 102 along with the non-absorbent layer 106 thus form a channel tending to maintain fluids within the absorbent layer 104.

Figure 5:
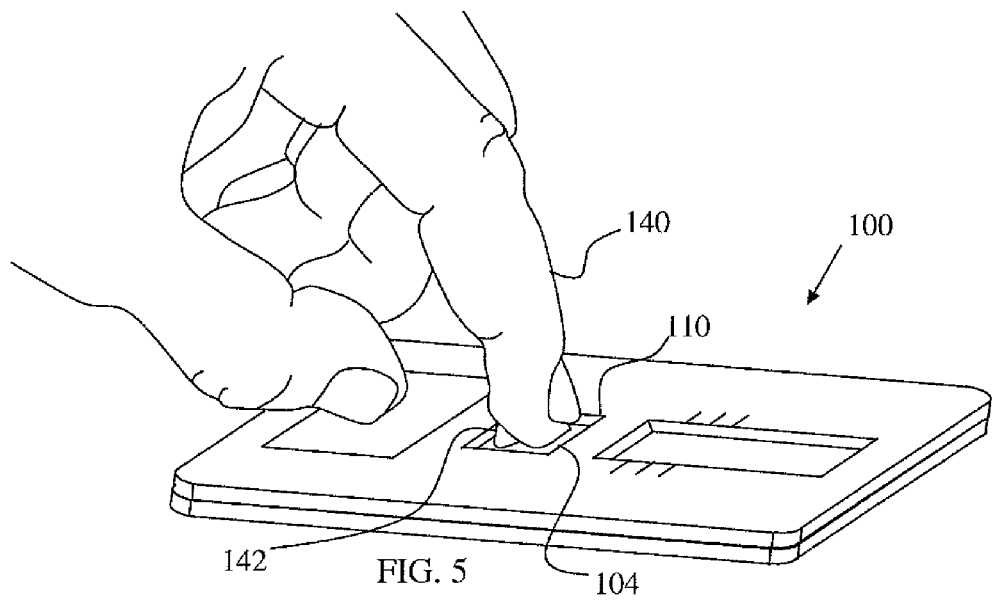
FIG. 5 depicts a perspective view of a patient providing a blood sample onto the absorbent layer of the separator card of FIG. 1 through a sample window.

The assembled separator card may be packaged for storage until a fluid sample is needed. A fluid sample may be obtained in a clinical or laboratory setting. Alternatively, the separator card 100 may be used by lay persons at virtually any location. A sample is obtained by producing the fluid, such as by pricking a finger to obtain blood. By way of example, a finger 140 has been lanced to obtain a blood sample 142 in FIG. 5. Drops of blood from the finger 140 are then dripped onto the absorbent layer 104 through the sample window 110 such that the blood sample 142 contacts the absorbent layer 104.

When the fluid sample contacts the absorbent layer 104, the sample is wicked by the absorbent layer 104, and preferentially aided in movement and separation by the chemical or physical nature of the non-absorbent layer 106, into the portion of the absorbent layer 104 viewable through the viewing window 112 along the channel formed by the compacted areas of the upper layer 102 along with the non-absorbent layer 106. As additional blood is placed into the portion of the absorbent layer 104 accessible through the sample window 110, the wicked fluid will become visible through the viewing window 112.

Figure 6:
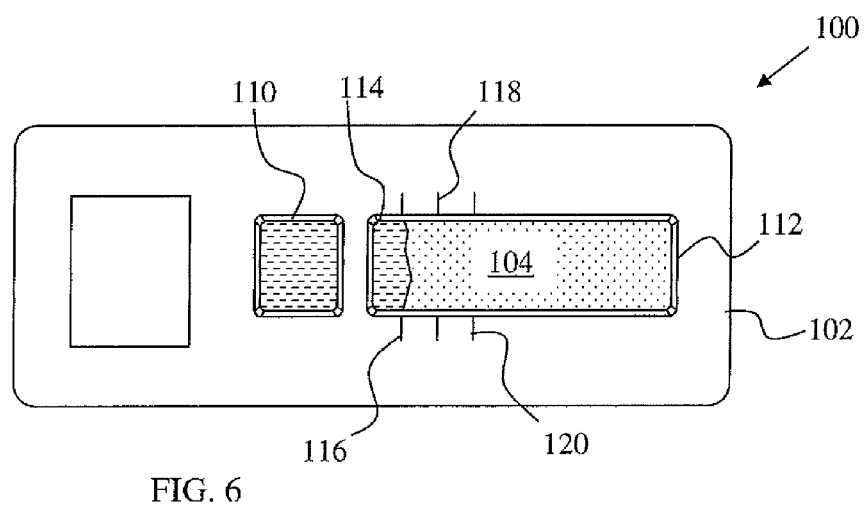
FIG. 6 depicts a top plan view of the separator card of FIG. 1 after sufficient fluid has been provided to the absorbent layer through the sample window to perform one test on a component of the fluid that will be separated by the absorbent layer in accordance with principles of the invention.

Once the fluid reaches the reference line 116 as shown in FIG. 6, sufficient blood has been absorbed to separate a quantity of plasma to perform a single test. The reference lines 118 and 120 may be provided to indicate when sufficient blood has been absorbed to separate a quantity of plasma necessary for performance of two tests and three tests, respectively.

The bridge 114 ensures a minimum spacing between the location at which the sample is deposited on the absorbent layer 104 and the reference lines 116, 118, and 120, thereby ensuring that a minimum volume of fluid has been placed into the absorbent layer 104. Thus, not only does the bridge 114 assist in maintaining the absorbent layer 104 within the separator card 100, the bridge 114 also assists in providing an accurate indication of the amount of fluid collected.

The amount of blood that is necessary to obtain the desired amount of plasma will vary based not only on the materials used, but also based upon the geometry of the channel formed. By way of example, using materials identified above absorbent layers may be formed with a width of from about 0.6 centimeters to about 4 centimeters. Optimum separation of plasma, however, is obtained with a width of about 1 centimeter. By optimizing the separation of the plasma, less blood is needed to obtain a particular amount of plasma.

The length of the absorbent layer 104 is also a consideration in ensuring sufficient separation of a sample fluid. By way of example, as the volume of sample fluid deposited in the absorbent layer 104 increases, the red blood cells, in the case of blood, will travel further along the absorbent layer 104. Thus, to ensure that a sufficient separation of a sample fluid occurs in the event too much sample is provided, the length of the absorbent layer 104 may be increased.

Figure 7:
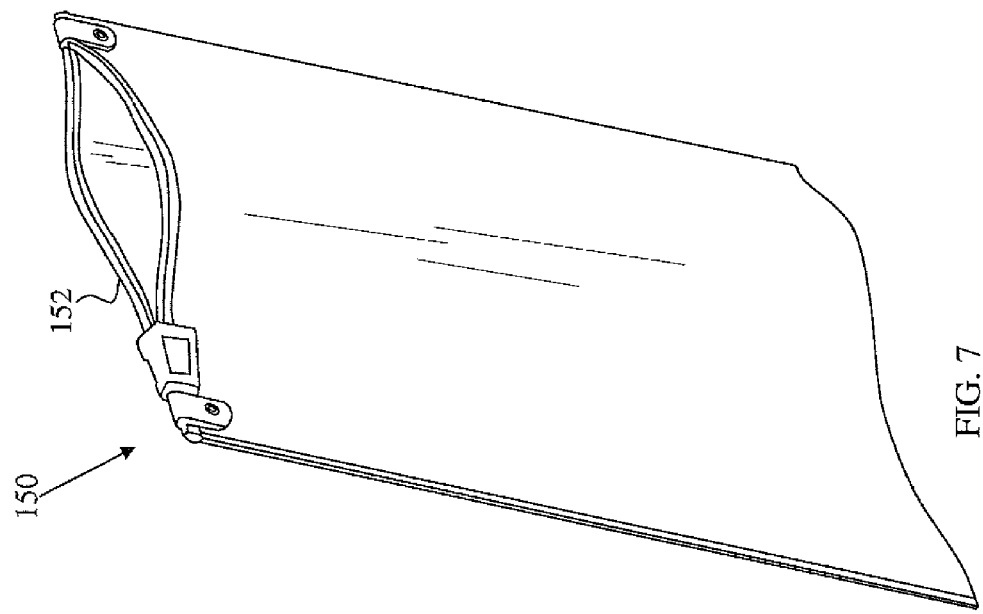
FIG. 7 depicts a perspective view of a resealable packet that may be used to transfer the separator card of FIG. 1 through a carrier service to a laboratory or other facility.

Once the desired sample has been collected, the separator card 100 is left to dry. The separator card may then be shipped via any desired mode of transportation to a processing facility. The dried fluid sample contained in the absorbent layer 104 may be stored for a relatively long time without undue degradation of the sample. Nonetheless, the shelf life of the sample may be extended by placement of the separator card 100 in a storage container such as the package 150 shown in FIG. 7.

The package 150 is a gas impermeable package such as a plastic or foil package. The package 150 includes a resealable opening 152. The resealable opening 152 may include a tamper proof mechanism to provide an indication that the package 150 has been opened after a sample has been sealed therein. The package 150 is sized to accept the separator card 100 therein, and may be further dimensioned to allow for insertion into a flat envelope of standard size for automated processing by a postal facility.

In one embodiment, an oxygen scrubber (not shown) is provided with the package 150. An oxygen scrubber typically includes thin shavings including pieces of metal and a carrier desiccant that loosely holds some amount of water. When the package 150 is sealed with an oxygen scrubber therein, oxygen present within the package 150 reacts with the metal in the presence of water to form rust, thereby binding the oxygen. Elimination of oxygen from the atmosphere of the package 150 provides increased stability for various components within the dried fluid sample. For example, lipid analytes such as HDL, cholesterol, and triglycerides may be further stabilized by removal of oxygen from the atmosphere in which the sample is stored.

If desired, the separator card 100 may be placed within the package 150 and the package 150 sealed before a fluid sample within the absorbent layer 104 has been dried. Sealing the package 150 with a wet fluid sample held in the separator card 100 inhibits drying of the sample.

Figure 8:
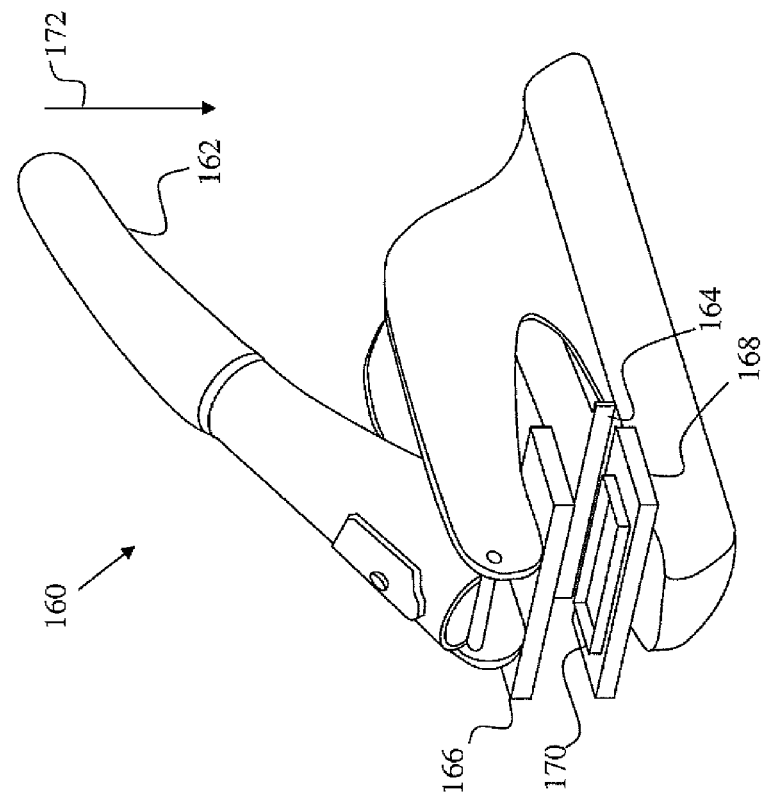
FIG. 8 depicts a perspective view of a removal tool that may be used to separate the absorbent strip of the separator card of FIG. 1.

Removal of the absorbent layer 104 from the separator card 100 for further processing is facilitated by the absence of an adherent between the absorbent layer 104 and any of the other components of the separator card 100. One device that may be used to remove the absorbent layer 104 is the removal tool 160 shown in FIG. 8. The removal tool 160 includes a lever arm 162, a guide stop 164, an upper mandrel 166 and a lower mandrel 168. The lower mandrel 168 includes a shaped cutting edge 170 which is sized to mate with the viewing window 112. The upper mandrel 166 includes a protuberance (not shown) that is slightly smaller than the viewing window 112 and positioned to fit within the shaped cutting edge 170.

Accordingly, removal of the portion of the absorbent layer 104 including the separated sample is accomplished by placement of the separator card 100 on the removal tool 160. Correct placement of the separator card 100 on the removal tool 160 may be guided by the guide stop 164. Alternatively, the viewing window 112 is simply positioned over the shaped cutting edge 170. Thereafter, movement of the lever arm 162 in the direction of the arrow 172 forces the protuberance (not shown) on the upper mandrel 166 against the support layer 108 at a location aligned with the viewing window 112. The absorbent layer viewable through the viewing window 112 is thus forced against the shaped cutting edge 170 which separates the portion of the absorbent layer 104 including the separated sample from the separator card 100.

If desired, the entire absorbent layer 104 may be removed from the separator card 100 by separating at least one end of the bridge 114 and applying sufficient force against the support layer 108 to deform the upper layer 102 sufficiently to allow the absorbent layer 104 to move past the rims or lips 134 and 136. A punch type device similar to the removal tool 160 may be used for this purpose.

Various other modifications of the separator card 100 may be incorporated to optimize the separator card for particular tests. In one embodiment, polyhexamethylene biguanide hydrochloride (PHMB) is incorporated into the absorbent layer 104. PHMB is an additive used in bandages for inhibiting the growth of microbial organisms such as bacteria and fungi.

In a further embodiment, prior to blood or other biological fluid application, a polypeptide fraction of highly purified dermal collagen of porcine origin (Prionex from Pentapharm) is applied and dried to the separator card absorbent layer 104. A separator card 100 treated with Prionex applied to the absorbent layer 104 at a 0.1 percent concentration can yield close to double the separation area of serum or plasma for a given volume of blood applied to the absorbent layer 104. Other substances such as various proteins, detergents, salts or solvents, or other chemicals may also be used to enhance separation of a sample fluid.

Another additive that is useful when obtaining fluid samples in the form of blood is sucrose. In particular, cholesterol containing molecules and cholesterol itself are hydrophobic molecules which in pure form do not mix with an aqueous solution. The complex arrangement of proteins, salts and carbohydrate and complex carbohydrate in blood, however, holds these hydrophobic molecules in suspension. Disruption of these serum components during drying could result in clumping or aggregation of the hydrophobic molecules rendering successful hydration of the hydrophobic molecules problematic.

Application of sucrose in 1 to 10% wt./vol. concentration followed by drying to the absorbent layer 104, however, provides a more reproducible drying and rehydration of cholesterol containing molecules such as HDL, LDL and the cholesterol molecule itself. It is believed that the carbohydrate sucrose molecules are surrounded by water molecules when a fluid sample is added. Thus, the sucrose layers surround the hydrophobic cholesterol or triglyceride molecules during the drying and inhibit aggregation via hydrophobic binding of the sucrose shielded hydrophobic molecules.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those skilled in the art. The invention in its broadest aspects is therefore not limited to the specific details, implementations, or illustrative examples shown and described. Accordingly, departures may be made from such details without departing from the spirit or scope of applicant's general inventive concept.

The invention claimed is:

1. A fluid sample collection card comprising:
an upper layer including a sample window and a viewing window extending therethrough, the viewing window spaced apart from the sample window;
an absorbent layer, having a width and a length, positioned beneath the upper layer and extending at least from directly beneath the sample window to directly beneath the viewing window; and
a non-absorbent layer positioned beneath the absorbent layer, the non-absorbent layer having a width and a length greater than the width and the length of the absorbent layer, wherein the upper layer is configured to indicate when a volume of fluid absorbed by the absorbent layer is sufficient to perform a test on at least one component in the fluid.

2. The card of claim 1, further comprising a first reference line adjacent to the viewing window, the first reference line associated with the volume of fluid, wherein the volume of fluid, when absorbed by the absorbent layer, separates into the at least one component along the length of the absorbent layer to an extent sufficient to perform the test on the at least one component.

3. The card of claim 2, further comprising a second reference line adjacent to the viewing window, the second reference line associated with a volume of fluid which, when absorbed by the absorbent layer, separates into at least one component along the length of the absorbent layer to an extent sufficient to perform two tests on the at least one component.

4. The card of claim 1, wherein the absorbent layer has a width of between about 0.6 centimeters and about 6 centimeters.

5. The card of claim 4, wherein the absorbent layer has a width of about 1 centimeter.

6. The card of claim 1, the absorbent layer comprising at least one additive for improving a characteristic of the absorbent layer.

7. The card of claim 6, wherein the at least one additive comprises polyhexamethylene biguanide hydrochloride (PHMB).

8. The card of claim 6, wherein the at least one additive comprises a dermal collagen of porcine origin.

9. The card of claim 6, wherein at least one additive comprises a carbohydrate material.

10. The card of claim 1, the non-absorbent layer comprising a fluoropolymer material.

11. A fluid sample collection device comprising:
an upper layer;
a first rim in the upper layer defining a first window with a length and a width through the upper layer;
a second rim in the upper layer defining a second window with a length and a width through the upper layer;
a bridge member with a length and a width located between the first window and the second window;
a non-absorbent layer with a length that is longer than the combined lengths of the first window, the second window and the bridge member; and
an absorbent layer clamped between the upper layer and the non-absorbent layer by at least one compacted area of the upper layer, the first rim, the second rim and the bridge, the absorbent layer extending at least from directly beneath the first window to directly beneath the second window, wherein the upper layer is configured to indicate when a volume of fluid absorbed by the absorbent layer is sufficient to perform a test on at least one component in the fluid.

12. The device of claim 11, wherein the first rim, the second rim, and the non-absorbent layer define a channel, the absorbent layer located within the channel.

13. The device of claim 11, wherein the first rim and the second rim each comprise the at least one compacted area of the upper layer.

14. The device of claim 11, further comprising a reference line adjacent to the viewing window, the reference line associated with an extent of the absorbent layer which can hold a volume of fluid sufficient to provide a sample of a component of the fluid after the component has been separated from the fluid by the absorbent layer.

15. A fluid sample collection device comprising:
an upper layer;
a sample receiving portion of an absorbent layer directly accessible through a first window in the upper layer;
a sample indicating portion of the absorbent layer viewable through a second window in the upper layer; and
a non-absorbent layer comprising a fluoropolymer material, and with a length that is longer than the combined lengths of the sample receiving portion of an absorbent layer and the sample indicating portion of the absorbent layer, the non-absorbent layer positioned on the side of the absorbent layer opposite to the upper layer, wherein the absorbent layer extends at least from directly beneath the first window to directly beneath the second window, and wherein the upper layer is configured to indicate when a volume of fluid absorbed by the absorbent layer is sufficient to perform a test on at least one component in the fluid.

16. The collection device of claim 15, the upper layer comprising:
a first rim defining the first window through the upper layer and positioned such that the sample receiving portion is accessible through the first window;
a second rim defining the second window through the upper layer and positioned such that the sample indicating portion is viewable through the second window; and
a bridge member located between the first window and the second window.

17. The collection device of claim 16, wherein the absorbent layer is clamped between the upper layer and the non-absorbent layer by the first rim, the second rim and the bridge.

18. The collection device of claim 16, further comprising a first reference line adjacent to the second window, the first reference line associated with a volume of fluid which, when absorbed by the absorbent layer, separates into at least one component along the length of the absorbent layer to an extent sufficient to perform a test on at least one component.

19. The collection device of claim 18, further comprising a second reference line adjacent to the second window, the second reference line associated with a volume of fluid which, when absorbed by the absorbent layer, separates into at least one component along the length of the absorbent layer to an extent sufficient to perform two tests on at least one component.

20. The collection device of claim 19, further comprising a third reference line adjacent to the second window, the third reference line associated with a volume of fluid which, when absorbed by the absorbent layer, separates into at least one component along the length of the absorbent layer to an extent sufficient to perform three tests on at least one component.

* * * * *